United States Patent [19]

Nevin

[11] Patent Number: 4,676,089
[45] Date of Patent: Jun. 30, 1987

[54] HUB FOR ROTATABLE TOOL

[76] Inventor: Donald M. Nevin, 3 Clearmeadow Ct., Woodbury, N.Y. 11797

[21] Appl. No.: 869,539

[22] Filed: Jun. 2, 1986

Related U.S. Application Data

[62] Division of Ser. No. 732,997, May 13, 1985, Pat. No. 4,624,876.

[51] Int. Cl.⁴ .............................................. B21D 53/26
[52] U.S. Cl. ...................................... 72/370; 29/159.3
[58] Field of Search .................. 72/370, 479; 403/193, 403/383; 29/159.3; 474/903

[56] References Cited

U.S. PATENT DOCUMENTS

| | | | |
|---|---|---|---|
| 1,331,156 | 2/1920 | Johnston et al. | 474/903 |
| 1,725,592 | 8/1929 | Mertes | 72/370 |
| 1,840,039 | 1/1932 | Joyce | 403/193 |
| 2,119,334 | 5/1938 | Leffler | 474/903 |
| 2,406,553 | 8/1946 | Mader | 403/383 |
| 2,464,323 | 3/1949 | Lee | 72/479 |
| 2,892,646 | 6/1959 | Doble | 403/383 |
| 3,884,066 | 5/1975 | Willmon | 72/479 |

Primary Examiner—Lowell A. Larson
Attorney, Agent, or Firm—Nolte, Nolte and Hunter

[57] ABSTRACT

A central hub for a rotatable tool which can be easily (a) mounted on a polygonal seat at one end of a rotatable mandrel for rotation of the tool with the mandrel and (b) subsequently removed with the tool from the seat of the mandrel. A central opening extending through the hub has a complex shape which includes a plurality of corners and a plurality of concave arcuate lines connecting the corners. The hub can be formed from a ductile preform having a generally cylindrical central opening extending through it by forcing, through the cylindrical opening in the preform, a polygonal punch having, in cross-section, substantially the same shape as, and a slightly larger size than, the polygonal cross-section of the seat of the mandrel which is to be inserted in the central opening in the hub of the tool.

4 Claims, 4 Drawing Figures

HUB FOR ROTATABLE TOOL

This is a division of application Ser. No. 732,997, filed May 13, 1985 now U.S. Pat. No. 4,624,876 granted Nov. 25, 1986.

BACKGROUND OF THE INVENTION

This invention relates to a tool which can be easily mounted on the end of a mandrel for rotation with the mandrel and subsequently removed when the tool has been worn out. This invention particularly relates to a novel hub construction for such a tool which facilitates the removal of the tool from the mandrel.

Separable rotatable tools, such as rotary brushes and abrasive discs, are well known in the dental and jewelry industries. See, for example, U.S. Pat. Nos. 1,837,938 and 4,055,897. Typically, such tools have been constructed with a central hub that is adapted to be mounted on the end of a rotatable mandrel or arbor. The hub generally has been provided with a central opening that has substantially the same cross-sectional shape (e.g., square or round) as a seat at the end of the mandrel and fits tightly about the mandrel's seat, so that the hub will rotate with the mandrel. In this regard, the central openings in the hubs of such tools have been made to fit about the seats at the ends of the mandrels so that the tools rotate closely with the ends of the mandrels and do not wobble or slide about the ends of the mandrels. With generally round hub openings and mandrel seats, this close fit has typically required that the hub receive the mandrel via a screw fastener or the like.

However, this close fit between the central openings in the tools' hubs and the mandrel's seats has tended to make it difficult to remove the tools from the mandrels when the tools have become worn out. This has been a particular problem in tools having relatively thick hubs (as measured along their axes of rotation). Relatively thick hubs have had to be made with central openings of generally round cross-sections, so that such hubs can be removed from their mandrels by simply removing their screw fasteners, which has nevertheless involved considerably inconvenience. There has been a need, therefore, for ways of providing a tight fit between the hubs, particularly thick hubs, of rotatable tools and their mandrels while allowing the tools to be removed from the mandrels with less inconvenience.

SUMMARY OF THE INVENTION

In accordance with this invention, a central hub for a rotatable tool is provided which can be easily (a) mounted on a polygonal seat at one end of a rotatable mandrel for rotation of the tool with the mandrel and (b) subsequently removed with the tool fron the seat of the mandrel. The hub has an improved central opening which extends through the hub along the axis of rotation of the tool and which has, in cross-section taken perpendicularly to the axis of rotation, a complex shape comprising:
  a plurality of corners and a plurality of concave arcuate lines connecting the corners; each corner being formed by a pair of intersecting generally straight lines and each arcuate line connecting the generally straight lines of a pair of adjacent corners; the corners, when connected by extending their straight lines, defining a polygon having substantially the same shape as, and a slightly larger size than, the polygonal cross-section of the seat of the mandrel.

In accordance with another aspect of this invention, a method is provided for forming the improved central opening in the hub of the rotatable tool, comprising the steps of:
  providing a ductile preform of the hub of the tool with a generally cylindrical central opening extending through the preform along the axis of rotation of the tool; and then
  urging a polygonal punch through the cylindrical opening in the preform along the axis of rotation of the tool; the punch having, in cross-section taken perpendicularly to the axis of rotation of the tool, substantially the same shape as, and a slightly larger size than, the polygonal cross-section of the seat of the mandrel which is to be inserted in the central opening in the hub of the tool.

DETAILED DESCRIPTION OF THE PREFERRED EMBODIMENT

Figure 1:
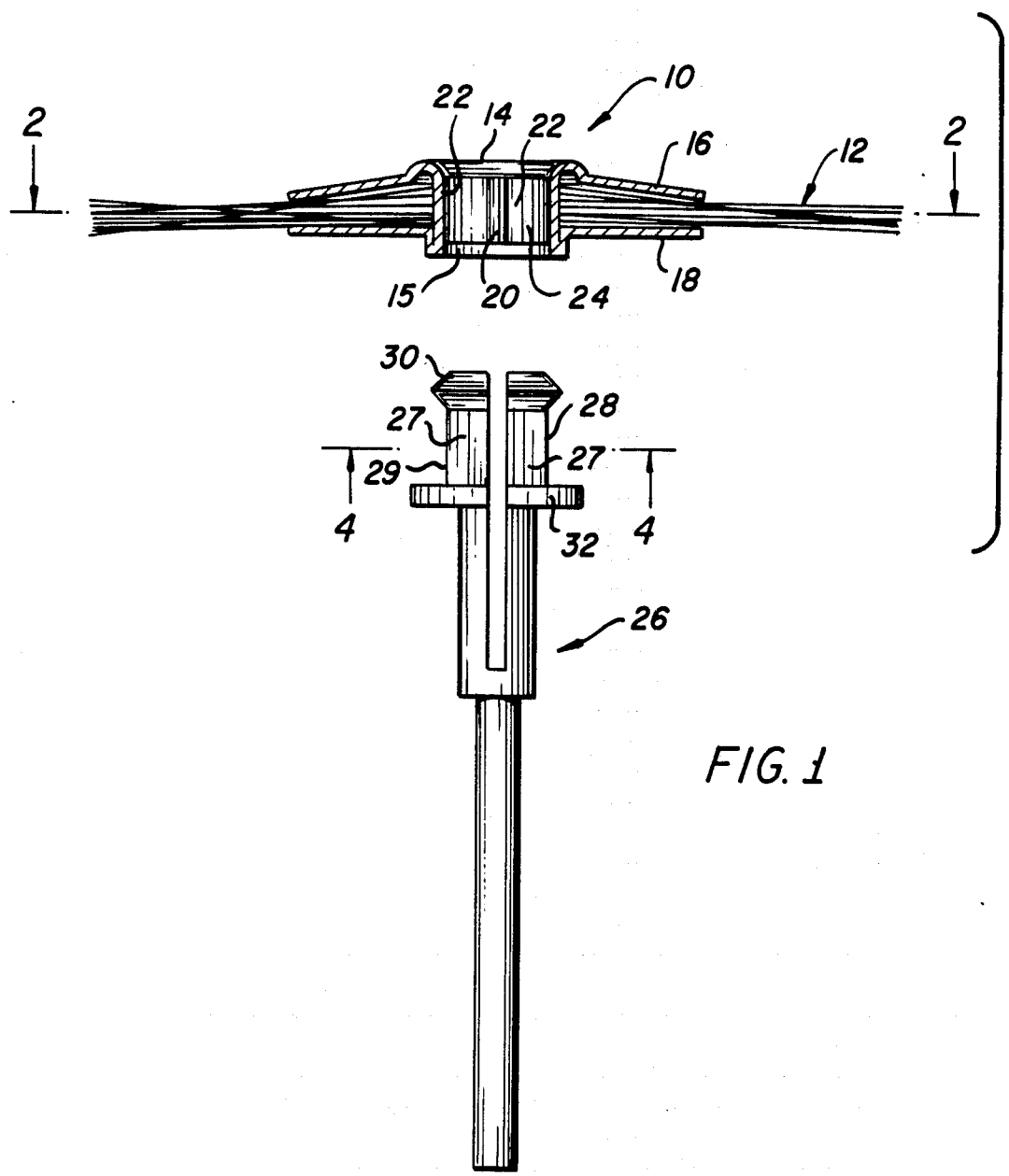
FIG. 1 is an exploded schematic elevation view of a rotatable tool of this invention and a rotatable mandrel on which the tool can be mounted and subsequently removed. The common axis of rotation of the tool and mandrel is vertical in FIG. 1. The tool in FIG. 1 is shown in the cross-section, taken along its axis of rotation.
Figure 2:
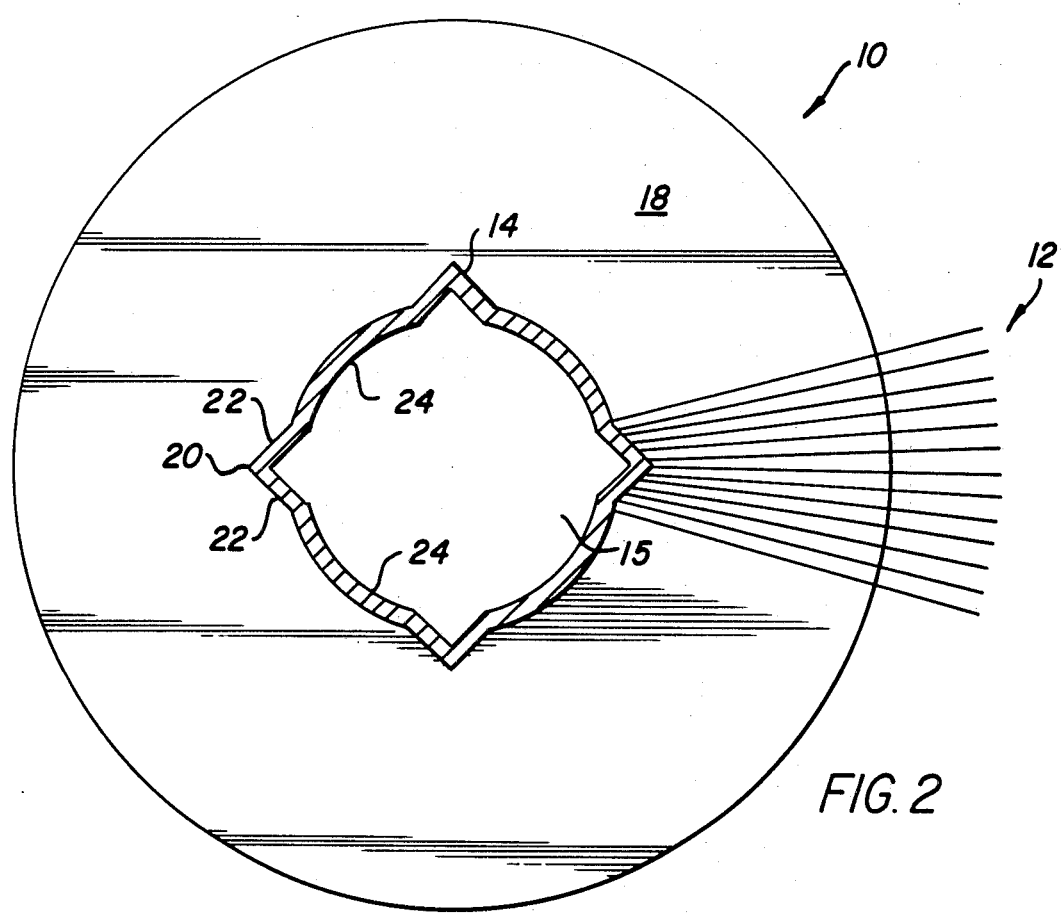
FIG. 2 is a sectional view, taken along line 2—2 in FIG. 1, showing the tool of this invention.
Figure 4:
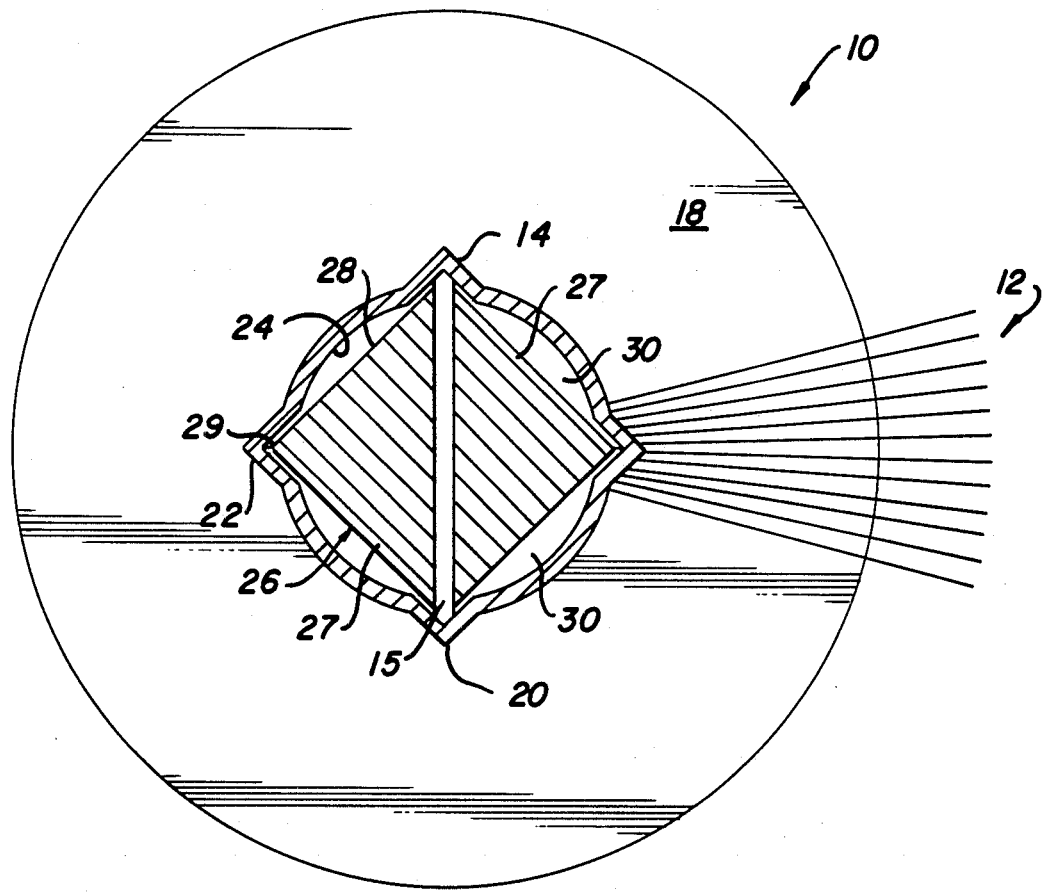
FIG.4 is a sectional view, taken along line 4—4 in FIG. 1, showing the tool of this invention mounted on the mandrel.

FIGS. 1, 2 and 4 schematically show a rotary brush, generally 10, in accordance with this invention. The brush 10 comprises a plurality of bristles 12 which can be made from conventional materials such as metal or plastic fibers or from animal hair. The bristles 12 extend radially outward from a central hub 14 having a central opening 15 extending through it. The central axis of the opening 15 in the hub 14 coincides with the axis of rotation of the hub 14 and the brush 10. The hub 14 is formed with two conventional annular flanges 16 and 18 at its top and bottom, respectively. One end of each bristle 12 is located between the flanges 16 and 18, and the free ends of the flanges 16 and 18 are crimped together to hold the bristles 12 between them in a conventional manner. In this regard, the hub 14 and its flanges 16 and 18 are preferably made from a relatively ductile material, such as a metal like brass or copper.

Figure 3:
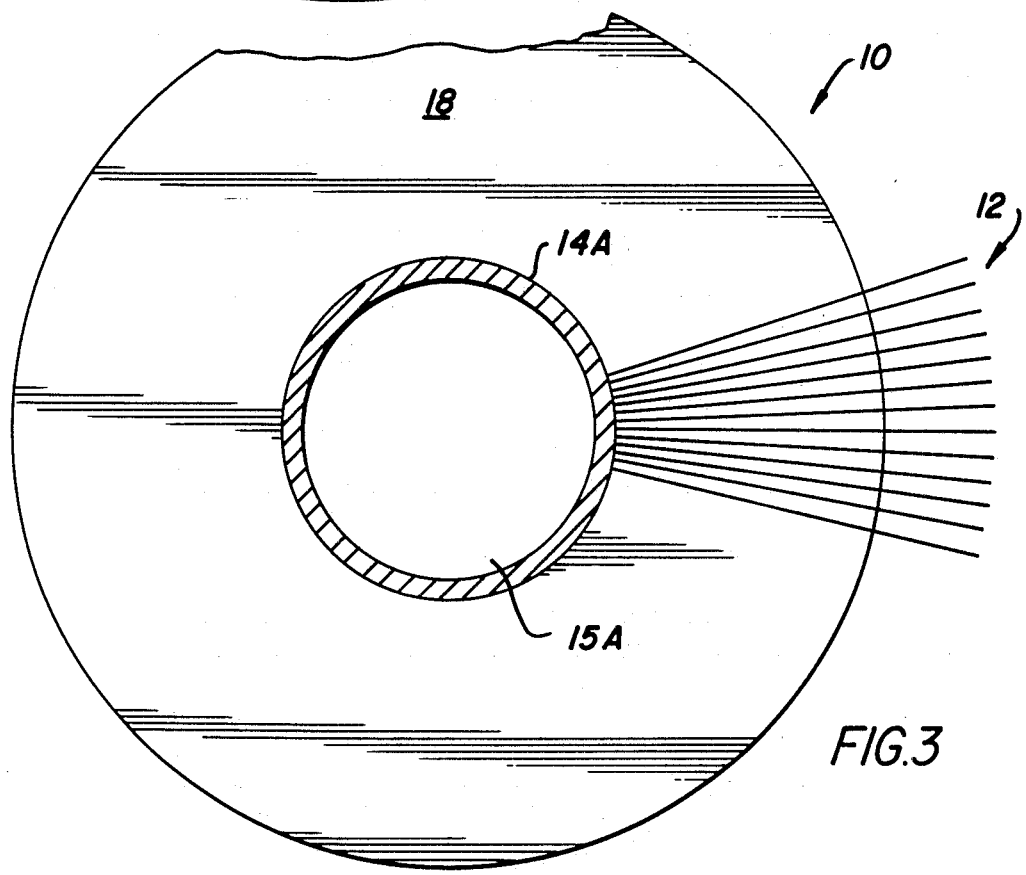
FIG. 3 is a sectional view, similar to FIG. 2, of a preform from which the tool of this invention, as shown in FIGS. 1 and 2, can be made.

The central opening 15 in the hub 14 of the brush 10 has a relatively complex shape when viewed in cross-section taken perpendicularly to the axis of rotation of the brush as in FIG. 2. The complex cross-sectional shape of the opening 15 can be suitably obtained by: providing a ductile preform 14A of the hub 14 with a generally cylindrical central opening 15A extending through the preform 14A along the axis of rotation of the brush 10 as shown in FIG. 3; and then urging a conventional square punch (not shown) through the generally cylindrical opening 15A along the coincident central axis of the opening 15A and axis of rotation of the brush 10. Urging the square punch through the generally cylindrical opening 15A in the ductile preform 14A of FIG. 3 in this way causes the four corners in the square cross-sectional shape of the punch to be impressed in the generally circular cross-sectional shape of the opening 15A and increases the radius of the arcuate portions of the cross-sectional shape of the opening 15A between the impressed corners. The resulting cross-sectional shape and size of the opening 15 in the hub 14, as schematically shown in FIG. 2, will vary depending upon the square cross-sectional area of the square punch which is utilized and the circular cross-sectional area of the cylindrical opening 15A in the hub preform 14A of FIG. 3 which is utilized. However, it is believed that the shape of the cross-section of the opening 15 of the hub 14 of FIG. 2 of this invention can be generally characterized as comprising four generally right angle corners 20, each formed by a pair of intersecting generally straight lines 22. The four corners 20 (when connected by extending their straight lines 22) define a square shape with the same size as the square cross-section of the square punch. The generally straight lines 22 of each adjacent pair of corners 20 of the opening 15 are connected by an arcuate line 24 that is concave when viewed from the center of the opening 15 and that has a larger radius than the cylindrical opening 15A of the preform 14A of FIG. 3.

The top end of a conventional rotatable mandrel 26, as shown in FIGS. 1 and 4, can be inserted into the central opening 15 of the hub 14 of the brush 10 with the axis of rotation of the mandrel 26 coinciding with the central axis of the opening 15 of the hub 14. Preferably, the top portions of the mandrel 26 are bifurcated, and the bifurcated portions 27 are spaced away from the axis of rotation of the mandrel 26. The bifurcated top portions 27 of the mandrel 26 include a seat 28 with a substantially square cross-sectional shape when viewed perpendicularly to the axis of rotation of the mandrel as in FIG. 4. The square cross-sectional shape of the seat 28 is slightly smaller than the square cross-sectional shape of the punch urged through the opening 15A in the ductile preform 14A to form the opening 15 in the hub 14. As a result, the seat 28 of the mandrel 26, with its generally right angle corners 29, can be inserted easily into the central opening 15 in the hub 14 and fit closely within the four corners 20 of the opening 15 in the hub 14, so that the hub 14 can rotate closely with the mandrel 26, without wobbling or sliding about the seat 28 of the mandrel. The mandrel seat 28 also can be easily removed from the hub's central opening 15, even if the hub 14 is relatively thick. In this regard, the fit between the central opening 15 in the hub 14 and the seat 28 of the mandrel 26 is tighter while the hub rotates with the mandrel than while the hub and mandrel are not rotating (e.g., when the hub 14 is being mounted on, or removed from, the mandrel 26). This effect is believed to be due to (1) enlargement of the separation between the bifurcated portions 27 of the mandrel 26 as a result of centrifugal forces on the mandrel portions 27 during rotation of the mandrel and (2) the engagement of the corners 20 and 29 of the hub opening 15 and the mandrel seat 28 during rotation of the mandrel and hub.

As shown in FIG. 1, the bifurcated top portions 27 of the mandrel 26 preferably also include a pair of conventional vertically spaced shoulders 30 and 32, respectively above and below the mandrel's seat 28. The mandrel's shoulders 30 and 32 have larger cross-sectional areas than the seat 28 so that the shoulders can hold the hub 14 of the brush 10 on the seat 28 of the mandrel 10. The upper shoulder 30 preferably has a substantially square cross-section and is downwardly and outwardly tapered at the top thereof to facilitate insertion of the bifurcated top portions 27 of the mandrel 26 into the hub's central opening 15. The space between the mandrel's bifurcated top portions 27 can be reduced by squeezing such top portions 27 together in a conventional manner in order to reduce the cross-sectional areas of the upper shoulder 30 and the seat 28 and thereby make it easier to insert the mandrel's seat 28 into the central opening 15 in the hub 14 of the brush 10 and to subsequently remove the mandrel's seat 28 from the hub opening 15.

It is thought that the invention and many of its attendant advantages will be understood from the foregoing description and it will be apparent that various changes can be made in the brush 10 and its hub 14 and in the method of forming the hub 14 and its central opening 15 from the ductile preform 14A without departing from the spirit and scope of the invention or sacrificing all of its material advantages, the brush 10 hereinbefore described being merely a preferred embodiment. For example, the cross-sectional shape of the central opening 15 in the hub 14 need not have four right angle corners 20 defining a square shape when the cross-sectional shape of the seat 28 of the mandrel 26 is not square. Indeed, the cross-sectional shape of the opening 15 can instead be formed with just three corners 20 or more than four corners which define a polygon by urging a polygonal (e.g, triangular, rectangular, hexagonal, etc.) punch through the generally cylindrical central opening 15A in the ductile preform 14A of the hub 14. However, the corners 20 of the opening 15 must define a polygon having substantially the same shape as, and only a slightly larger size than, the polygonal cross-section of the seat 28 of the mandrel 26, so that the corners 20 of the opening 15 will fit closely about the corners 29 of the seat 28 and, as a result, the hub 14 and brush 10 will rotate closely with the mandrel 26, without wobbling or sliding about the seat 28 of the mandrel. Preferably, the central opening 15 in the hub 14 is formed with a regular polygonal punch so that the angles formed by the corners 20 of the opening 15 are equal angles.

I claim:

1. A method for forming a central opening in a central hub of a rotable tool which allows the hub to be easily (a) mounted on a polygonal seat at one end of a rotatable mandrel for rotation of the tool with the mandrel and (b) subsequently removed with the tool from the seat of the mandrel, comprising the steps of:

providing a ductile preform of the hub of the tool with a generally cylindrical central opening extending through the preform along the axis of rotation of the tool; and then urging a polygonal punch through the cylindrical opening in the preform along the axis of rotation of the tool; the punch having, in cross-section taken perpendicularly to the axis of rotation of the tool, substantially the same shape as, and a slightly larger size than, the polygonal cross-section of the seat of the mandrel;

the central opening being formed in the hub with a complex shape comprising a plurality of corners and a plurality of concave arcuate lines connecting the corners; each corner being formed by substantially only a pair of intersecting generally straight lines and each arcuate line connecting the generally straight lines of a pair of adjacent corners; the corners, when connected by extending their straight lines, defining a polygon having substantially the same shape as, and a slightly larger size than, the polygonal cross-section of the seat of the mandrel; every straight line of each corner being connected to another straight line by an arcuate line; ad every corner extending axially through the central opening, parallel to its axis of rotation.

2. The method of claim 1, wherein the punch is a regular polygonal punch.

3. The method of claim 2, wherein the punch is a rectangular punch.

4. The method of claim 3, wherein the punch is a square punch.

* * * * *